DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED AUGUST 14, 1973

913 O.G. 392

T913,001

PROCESS FOR THE PREPARATION OF 2-STYRYLBENZOXAZOLES AND 2 - STYRYLBENZOTHIAZOLES

Robert D. Burpitt, 1405 Van Oaks Drive 37665, and Robert H. Hasek, 4503 Mitchell Road 37664, both of Kingsport, Tenn.

Filed Apr. 17, 1972, Ser. No. 244,936
Int. Cl. C07d *85/48*
U.S. Cl. 260—240 D
No Drawing. 9 Pages Specification

This invention relates to a process for the preparation of 2-styrylbenzoxazoles and 2-styrylbenzothiazoles by the condensation of a 2-methylbenzoxazole or 2-methylbenzothiazole with an aryl aldehyde or thienyl aldehyde in the presence of a catalyst system comprising a sulfonic acid and an N-alkylpyrrolidone.